US011051930B2

(12) United States Patent
Mochizuki et al.

(10) Patent No.: US 11,051,930 B2
(45) Date of Patent: Jul. 6, 2021

(54) MEMBRANE FOR IMMUNOISOLATION, CHAMBER FOR TRANSPLANTATION, AND DEVICE FOR TRANSPLANTATION

(71) Applicant: FUJIFILM Corporation, Tokyo (JP)

(72) Inventors: Yusuke Mochizuki, Ashigarakami-gun (JP); Kentaro Nakamura, Ashigarakami-gun (JP); Shigeaki Ohtani, Ashigarakami-gun (JP); Naohiro Matsunaga, Ashigarakami-gun (JP); Ryuta Takegami, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/409,241

(22) Filed: May 10, 2019

(65) Prior Publication Data

US 2019/0262122 A1 Aug. 29, 2019

Related U.S. Application Data

(63) Continuation of application No. PCT/JP2017/040339, filed on Nov. 9, 2017.

(30) Foreign Application Priority Data

Nov. 11, 2016 (JP) .............................. JP2016-220201

(51) Int. Cl.
*A61F 2/02* (2006.01)
*A61L 27/16* (2006.01)
(Continued)

(52) U.S. Cl.
CPC ................ *A61F 2/022* (2013.01); *A61F 2/02* (2013.01); *A61K 35/12* (2013.01); *A61K 38/28* (2013.01);
(Continued)

(58) Field of Classification Search
None
See application file for complete search history.

(56) References Cited

U.S. PATENT DOCUMENTS

| 4,933,081 A | 6/1990 | Sasaki et al. |
| 5,807,406 A | 9/1998 | Brauker et al. |
| (Continued) | | |

FOREIGN PATENT DOCUMENTS

| CA | 2959291 A1 | 3/2016 |
| CN | 101528156 A | 9/2009 |
| (Continued) | | |

OTHER PUBLICATIONS

International Preliminary Report on Patentability and Written Opinion of the International Searching Authority(Forms PCT/IB/326, PCT/IB/373 and PCT/ISA/237), dated May 23, 2019, for International Application No. PCT/JP2017/040339, with an English Translation of the Written Opinion.
(Continued)

*Primary Examiner* — Dominic Lazaro
(74) *Attorney, Agent, or Firm* — Birch, Stewart, Kolasch & Birch, LLP

(57) ABSTRACT

According to the present invention, there are provided a membrane for immunoisolation, including: a porous membrane that contains a polymer, in which the porous membrane includes a layered compact portion where a pore diameter is the smallest within the membrane, and a pore diameter continuously increases in a thickness direction from the compact portion toward at least one surface of the porous membrane; a chamber for transplantation for enclosing a biological constituent therein, including the above-described membrane for immunoisolation on at least a part of a surface forming an inside and an outside of the chamber for transplantation; and a device for transplantation, including the above-described chamber for transplantation enclos-
(Continued)

ing the biological constituent therein. In the membrane for immunoisolation of the present invention which can be manufactured at low costs, a deterioration in substance permeability is unlikely to occur.

20 Claims, 6 Drawing Sheets

(51) Int. Cl.
| | | |
|---|---|---|
| *A61L 27/18* | (2006.01) | |
| *A61L 27/38* | (2006.01) | |
| *A61L 31/04* | (2006.01) | |
| *A61L 31/14* | (2006.01) | |
| *A61K 35/12* | (2015.01) | |
| *A61K 38/28* | (2006.01) | |

(52) U.S. Cl.
CPC ............ *A61L 27/16* (2013.01); *A61L 27/18* (2013.01); *A61L 27/38* (2013.01); *A61L 31/04* (2013.01); *A61L 31/14* (2013.01); *A61K 2035/122* (2013.01); *A61K 2035/128* (2013.01)

(56) References Cited

U.S. PATENT DOCUMENTS

| | | | |
|---|---|---|---|
| 5,871,767 | A | 2/1999 | Dionne et al. |
| 6,060,640 | A | 5/2000 | Pauley et al. |
| 2007/0154524 | A1 | 7/2007 | Kauper et al. |
| 2010/0209468 | A1 | 8/2010 | Kennedy et al. |
| 2011/0210067 | A1 | 9/2011 | Kato et al. |
| 2016/0120932 | A1 | 5/2016 | Iwata et al. |
| 2016/0228473 | A1 | 8/2016 | Iwata et al. |
| 2017/0266626 | A1 | 9/2017 | Kayama et al. |
| 2017/0348650 | A1* | 12/2017 | Kayama ................ B01D 69/02 |

FOREIGN PATENT DOCUMENTS

| | | | | |
|---|---|---|---|---|
| CN | 105561396 | A | 5/2016 | |
| CN | 105764538 | A | 7/2016 | |
| EP | 0747046 | A2 | 12/1996 | |
| JP | 62-27006 | A | 2/1987 | |
| JP | 6-507412 | A | 8/1994 | |
| JP | 10-507111 | A | 7/1998 | |
| JP | 2009-522269 | A | 6/2009 | |
| JP | 2015-110194 | A | 6/2015 | |
| WO | WO 92/07525 | A1 | 5/1992 | |
| WO | WO 2008/027420 | A2 | 3/2008 | |
| WO | WO 2008/112190 | A1 | 9/2008 | |
| WO | WO 2016-031834 | A1 | 3/2016 | |
| WO | WO 2016/117565 | A1 | 7/2016 | |
| WO | WO-2016117565 | A1 * | 7/2016 | ............. B01D 69/08 |

OTHER PUBLICATIONS

International Search Report, dated Jan. 9, 2018, for International Application No. PCT/JP2017/040339, with an English translation.
Tatarkiewicz, et al., "Reversal of Hyperglycemia in Mice After Subcutaneous Transplantation of Macroencapsulated Islets", Transplantation, vol. 67, No. 5, Mar. 15, 1999, pp. 665-671 (7 pages).
Extended European Search Report for corresponding European Application No. 17869451.9, dated Oct. 15, 2019.
Japanese Office Action, dated Mar. 31, 2020, for corresponding Japanese Application No. 2018-550239, with an English machine translation.
Chinese Office Action and Search Report for corresponding Chinese Application No. 201780069833.5, dated Feb. 2, 2021, with English translation of the Office Action.

* cited by examiner

POROUS MEMBRANE 14

POROUS MEMBRANE 15

MEMBRANE FOR IMMUNOISOLATION, CHAMBER FOR TRANSPLANTATION, AND DEVICE FOR TRANSPLANTATION

CROSS-REFERENCE TO RELATED APPLICATIONS

This application is a continuation of PCT International Application No. PCT/JP2017/040339 filed on Nov. 9, 2017, which claims priority under 35 U.S.C. § 119 (a) to Japanese Patent Application No. 2016-220201 filed on Nov. 11, 2016, the entire content of which is incorporated herein by reference.

BACKGROUND OF THE INVENTION

1. Field of the Invention

The present invention relates to a membrane for immunoisolation. The present invention further relates to a chamber for transplantation which has the membrane for immunoisolation, and a device for transplantation.

2. Description of the Related Art

Immunoisolation is one of methods for preventing immune reactions in a recipient during transplantation of biological components such as cells, tissues, or organs. A membrane for immunoisolation is a selectively permeable membrane which allows water, oxygen, glucose, or the like to permeate, and which, at the same time, performs immunoisolation by inhibiting permeation of immune cells and the like involved in an immune rejection. For example, while preventing an immune rejection, it is possible to achieve a purpose of transplantation by a device for transplantation utilizing a membrane for immunoisolation which allows physiologically active substances to permeate therethrough, for transplantation of cells secreting the physiologically active substances.

In order to allow continuous supplying of nutrients to transplanted biological constituents and secretion of physiologically active substances from the transplanted biological constituents, the vascular plexus is preferably formed around a device for transplantation. A case where the vascular plexus is not formed and thus the device for transplantation is encapsulated by fibroblasts, can lead to necrosis of biological constituents. Such a characteristic in formation of the vascular plexus is shown to depend on a microstructure of a membrane for immunoisolation. JP1998-507111A (JP-H10-507111A) discloses, as a membrane for immunoisolation having a structure that contributes to promoting the formation of the vascular plexus, a porous membrane formed by laminating a plurality of polyimide polymer films in which pores are formed by lithography or etching. In addition, Transplantation, 67, 665 (1995) discloses that transplantation is performed using a commercially available chamber for transplantation (TheraCyte (registered trade name)), the chamber being formed by using a porous membrane that is a laminate membrane obtained by laminating a membrane having a pore diameter of 0.45 μm and cell retention properties and an outer membrane of polytetrafluoroethylene (PTFE) having a pore diameter of 5 μm; and that this outer membrane induced the formation of new blood vessels in tissue of a recipient.

SUMMARY OF THE INVENTION

The method disclosed in JP1998-507111A (JP-H10-507111A) requires fine manufacturing, and thus tends to manufacture defective products. In addition, the membrane for immunoisolation disclosed in both JP1998-507111A (JP-H10-507111A) and Transplantation, 67, 665 (1995) also requires a plurality of layers to be laminated, easily leading to an increase in cost. Furthermore, in the membrane for immunoisolation in which pore diameters on a surface are small as disclosed in Transplantation, 67, 665 (1995), a deterioration in substance permeability is likely to occur in general due to adsorption of proteins or the like.

An object of the present invention is to provide a membrane for immunoisolation which can be manufactured at low costs, in which a deterioration in substance permeability is unlikely to occur.

The inventors of the present invention have conducted intensive studies to achieve the above-mentioned object, have found a microstructure of a membrane for immunoisolation, in which a deterioration in substance permeability is unlikely to occur, and therefore have completed the present invention based on these findings.

That is, the present invention provides the following <1> to <18>.

<1> A membrane for immunoisolation, comprising:
a porous membrane that contains a polymer,
in which the porous membrane includes a layered compact portion where a pore diameter is smallest within the membrane, and
a pore diameter continuously increases in a thickness direction from the compact portion toward at least one surface of the porous membrane.

<2> The membrane for immunoisolation according to claim 1, which is made from the porous membrane.

<3> The membrane for immunoisolation according to <1> or <2>, in which the porous membrane has a minimum pore diameter of 0.02 μm to 1.5 μm.

<4> The membrane for immunoisolation according to <1> or <2>, in which the porous membrane has a minimum pore diameter of 0.02 μm to 1.3 μm.

<5> The membrane for immunoisolation according to any one of <1> to <4>, in which a ratio of a minimum pore diameter to a maximum pore diameter of the porous membrane is 3.0 to 20.0.

<6> The membrane for immunoisolation according to any one of <1> to <5>, in which the compact portion has a thickness of 0.5 μm to 30 μm.

<7> The membrane for immunoisolation according to any one of <1> to <6>, in which the porous membrane has a thickness of 10 μm to 250 μm.

<8> The membrane for immunoisolation according to any one of <1> to <7>, in which the porous membrane contains at least one kind of polysulfone and polyvinylpyrrolidone.

<9> The membrane for immunoisolation according to any one of <1> to <8>, in which the compact portion is located between any one surface X of the porous membrane and a portion at a distance of one-third the thickness of the porous membrane from the surface X.

<10> The membrane for immunoisolation according to any one of <1> to <8>, in which the compact portion is located between any one surface X of the porous membrane and a portion at a distance of two-fifths the thickness of the porous membrane from the surface X.

<11> The membrane for immunoisolation according to <10>, in which a pore diameter continuously increases in the thickness direction from the compact portion toward at least a surface opposite to the surface X of the porous membrane.

<12> The membrane for immunoisolation according to <11>, in which a pore diameter continuously increases in the thickness direction from the compact portion toward both surfaces of the porous membrane.

<13> A chamber for transplantation for enclosing a biological constituent therein, the chamber comprising:

the membrane for immunoisolation according to any one of <1> to <12> on at least a part of a surface forming an inside and an outside of the chamber for transplantation.

<14> A chamber for transplantation for enclosing a biological constituent therein, the chamber comprising:

the membrane for immunoisolation according to any one of <9> to <12> on at least a part of a surface forming an inside and an outside of the chamber for transplantation, in which the surface X of the porous membrane is on the inside.

<15> The chamber for transplantation according to <13> or <14>, in which the biological constituent is a cell.

<16> A device for transplantation, comprising the chamber for transplantation according to any one of <13> to <15> enclosing the biological constituent therein.

<17> The device for transplantation according to <16>, in which the biological constituent releases a physiologically active substance.

<18> The device for transplantation according to <17>, in which the physiologically active substance is insulin.

According to the present invention, it is possible to provide a membrane for immunoisolation which can be manufactured at low costs, in which a deterioration in substance permeability is unlikely to occur. A device for transplantation including a chamber for transplantation which has the membrane for immunoisolation of the present invention and encloses a biological constituent therein, is unlikely to receive an immune rejection after transplantation into a recipient, and thus can be used for a long period of time.

DESCRIPTION OF THE PREFERRED EMBODIMENTS

Figure 1:
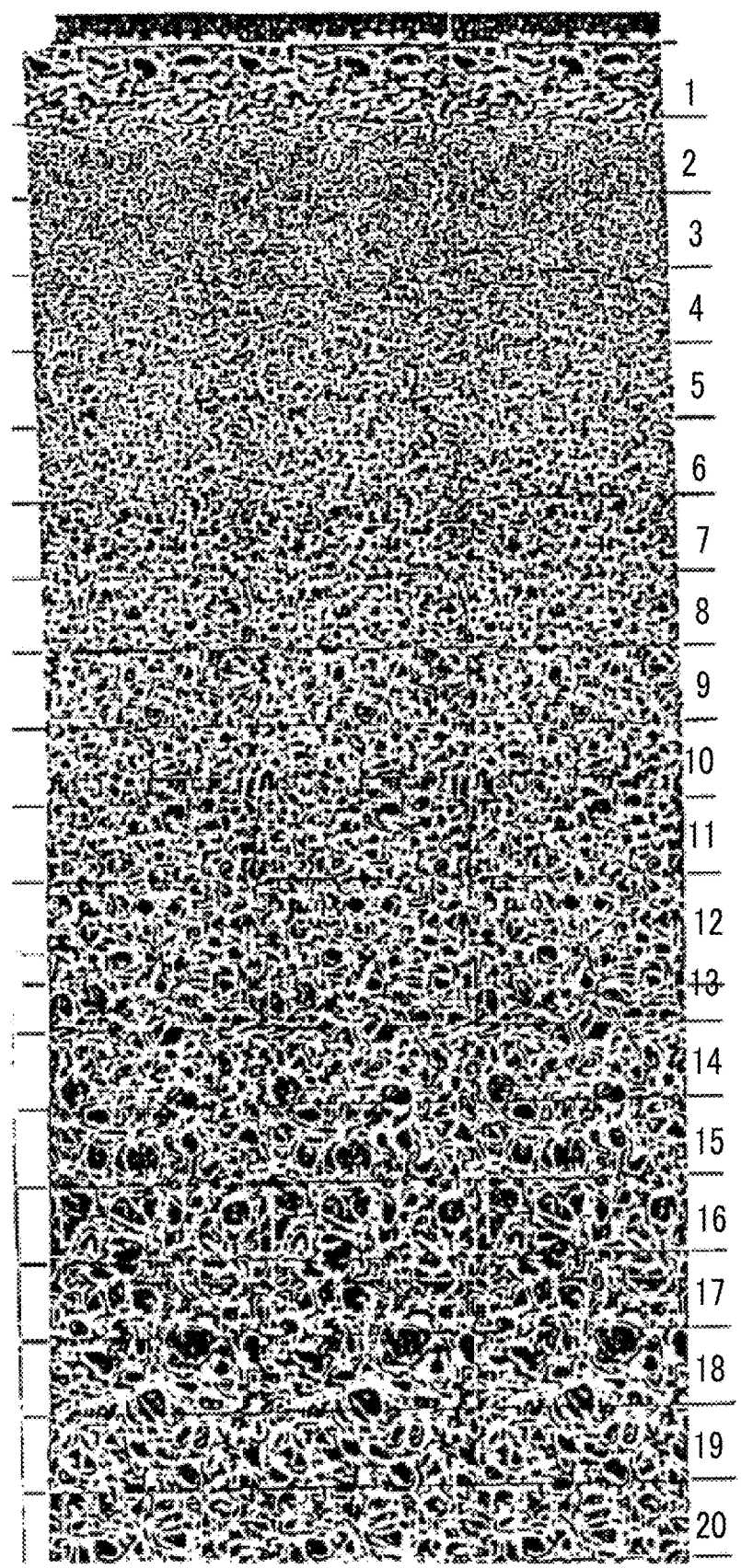
FIG. 1 is a view showing an SEM image of a cross section of a porous membrane 3 (membrane for immunoisolation) obtained in Examples.

Hereinafter, the present invention will be described in detail.

In the present specification, "to" is used to refer to a meaning including numerical values denoted before and after "to" as a lower limit value and an upper limit value.

<Membrane for Immunoisolation>

In the present specification, a membrane for immunoisolation refers to a membrane used for immunoisolation.

Immunoisolation is a method for preventing an immune rejection. In general, immunoisolation is one of a method for preventing an immune rejection by a recipient in a case of transplantation. Here, the immune rejection is a rejection by a recipient with respect to a biological constituent to be transplanted. A biological constituent is isolated from an immune rejection by a recipient due to immunoisolation. Examples of immune rejections include reactions due to cellular immune responses and reactions due to humoral immune responses.

The membrane for immunoisolation is a selectively permeable membrane that allows nutrients such as oxygen, water, and glucose to permeate therethrough, and inhibits permeation of immune cells and the like involved in an immune rejection. Examples of immune cells include macrophages, dendritic cells, neutrophils, eosinophils, basophils, natural killer cells, various T cells, B cells, and other lymphocytes.

Depending on the application, the membrane for immunoisolation of the embodiment of the present invention preferably inhibits permeation of high-molecular-weight proteins such as immunoglobulins (IgM, IgG, and the like) and complements, and preferably allows a relatively low-molecular-weight physiologically active substances such as insulin to permeate therethrough.

The selective permselectivity of the membrane for immunoisolation may be adjusted according to the application. The membrane for immunoisolation of the embodiment of the present invention may be a selectively permeable membrane which blocks a substance having a molecular weight such as 500 kDa or more, 100 kDa or more, 80 kDa or more, or 50 kDa or more. For example, it is preferable that the membrane for immunoisolation be capable of inhibiting permeation of the smallest IgG (molecular weight of about 160 kDa) among antibodies. In addition, the membrane for immunoisolation of the embodiment of the present invention may be a selectively permeable membrane which blocks a substance having a diameter such as 500 nm or more, 100 nm or more, 50 nm or more, or 10 nm or more, as a sphere size.

The membrane for immunoisolation of the embodiment of the present invention includes a porous membrane containing a polymer. The membrane for immunoisolation of the embodiment of the present invention may formed of only the porous membrane or may contain other layers. Examples of other layers include a hydrogel membrane. The membrane for immunoisolation of the embodiment of the present invention may have a protective film, which is easily peelable, on the surface thereof for transportation or the like.

A thickness of the membrane for immunoisolation of the embodiment of the present invention is not particularly limited, but may be 10 μm to 500 μm, is preferably 20 μm to 300 μm, and is more preferably 30 μm to 250 μm. In particular, the thickness of the membrane for immunoisolation of the embodiment of the present invention is more preferably 10 μm to 200 μm, is even more preferably 10 μm to 100 μm, and is particularly preferably 10 μm to 50 μm.

[Porous Membrane]

(Structure of Porous Membrane)

The porous membrane is a membrane having a plurality of pores. Pores can be confirmed by, for example, captured images of a scanning electron microscope (SEM) or captured images of a transmission electron microscope (TEM) of a cross section of the membrane.

A thickness of the porous membrane is not particularly limited, but may be 10 µm to 250 µm, is preferably 20 µm to 220 µm, and is more preferably 30 µm to 200 µm. In particular, the thickness of the porous membrane is more preferably 10 µm to 200 µm, is even more preferably 10 µm to 100 µm, and is particularly preferably 10 µm to 50 µm. By setting the thickness of the porous membrane to 10 µm or more, it is possible to obtain membrane hardness at which the chamber for transplantation does not break in a recipient. In addition, by setting the thickness of the porous membrane to 250 µm or less, it is possible to obtain the chamber for transplantation having stiffness to the extent that a recipient is not uncomfortable.

In the membrane for immunoisolation of the embodiment of the present invention, the porous membrane has, within the membrane, a layered compact portion where a pore diameter becomes smallest, and a pore diameter continuously increases in a thickness direction from this compact portion toward at least one surface of the porous membrane. The pore diameter is determined by an average pore diameter of a section or a parting line which will be described later. The pore diameter means a diameter of pores.

The surface of the membrane means a main surface (a front surface or a back surface showing an area of the membrane), and does not mean a surface in the thickness direction of an end of the membrane. The surface of the porous membrane may be an interface with another layer. In the membrane for immunoisolation of the embodiment of the present invention, it is preferable that the porous membrane have almost the same structure in an intra-membrane direction (a direction parallel to the membrane surface) with respect to pore diameters, and in the entire area with respect to pore diameter distributions (a difference in pore diameters in the thickness direction).

With the porous membrane having pore diameter distribution in the thickness direction, the life of the membrane for immunoisolation of the embodiment of the present invention can be improved. The reason is that, by using a plurality of membranes having substantially different pore diameters, effects are obtained as though multistage filtration would be carried out, and therefore a deterioration in the membrane can be prevented.

A pore diameter may be measured from a photograph of a cross section of the membrane obtained by an electron microscope. The porous membrane can be cut with a microtome or the like, and it is possible to obtain a photograph of a cross section of the porous membrane as a section of a thin membrane which a cross section can be observed.

In the present specification, comparing pore diameters in the thickness direction of the membrane having a thickness greater than 100 µm is performed by dividing an SEM image of the cross section of the membrane in the thickness direction of the membrane. The number of divisions can be appropriately selected from a thickness of the membrane. The number of divisions is at least 5 or more, and for example, in a case of a membrane having a thickness of 200 µm, the membrane is divided into 20 parts from a surface X to be described later. A size of a division width means a size of a width in the thickness direction of the membrane, and does not mean a width size in a photograph. In the comparison of pore diameters in the thickness direction of the membrane, pore diameters are compared as an average pore diameter of each section. An average pore diameter of each section may be, for example, an average value of 50 pores in each section of a cross-sectional view of the membrane. The cross-sectional view of the membrane in this case may be obtained with a width of 80 µm (a distance of 80 µm in a direction parallel to a surface), for example. In this case, for a section in which pores are large and therefore only less than 50 pores can be measured, it is sufficient that an average pore diameter be an average pore diameter obtained by measuring the available number of pores that can be counted in that section. In addition, in this case, in a case where pores are too large to fit in this section, a size of pore is measured over another section.

The layered compact portion having the smallest pore diameter refers to a layered portion of the porous membrane corresponding to a section having the smallest average pore diameter among sections of the membrane cross section. The compact portion may be formed of a portion corresponding to one section, or may be formed of portions corresponding to a plurality of sections having an average pore diameter 1.1 times or less an average pore diameter of the section having the smallest average pore diameter such as 2 or 3.

In the present specification, the comparison of pore diameters in the thickness direction of the membrane having a thickness of 100 µm or less is performed by comparing pore diameters in 19 parting lines in a case where an SEM image of the membrane cross section is divided into 20 in the thickness direction of the membrane. 50 or more consecutive pores that intersect or are in contact with the parting line are selected, each of pore diameters are measured, and an average value is calculated as an average pore diameter. Here, as the pore diameter, not a length of a portion where the selected pore intersects the parting line, but a diameter is used, the diameter being calculated using an area, which is obtained by calculating an area of pores calculated from an SEM image of the membrane cross section by image processing, as an area of a true circle. In this case, for a parting line in which pores are large and therefore only up to 50 pores can be selected, an average pore diameter is assumed to an average pore diameter obtained by measuring 50 pores by broadening the field of view of an SEM image for obtaining the membrane cross section. Pore diameters in the thickness direction of the membrane are compared by comparing the obtained average pore diameter for each parting line.

Even in a case where pore diameters in the thickness direction of the membrane having a thickness of more than 100 µm compared using a parting line, a structure of the porous membrane can be determined as in the case of using the division as described above.

The layered compact portion having the smallest pore diameter refers to a layered portion of the porous membrane including the parting line where an average pore diameter becomes smallest among parting lines in a photograph of the membrane cross section. The compact portion may include two or more parting lines. For example, in a case where two or more parting lines, which have an average pore diameter 1.1 times or less the minimum average pore diameter, are consecutive, the compact portion is assumed to include two or more consecutive parting lines. In the present specification, a thickness of the compact portion is a product of the number of parting lines included in the compact portion and one twentieth of the thickness of the membrane.

A thickness of the compact portion may be 0.5 µm to 50 µm, and is preferably 0.5 µm to 30 µm. In the present specification, an average pore diameter of the compact portion is denoted as the minimum pore diameter of the porous membrane. The minimum pore diameter of the porous membrane is preferably 0.02 µm to 1.5 µm, and is more preferably 0.02 µm to 1.3 µm. The reason is that the minimum pore diameter of such a porous membrane can inhibit permeation of at least normal cells. Here, an average pore diameter of the compact portion can also be measured by ASTM F316-80.

The porous membrane has a compact portion within the membrane. The phrase "within the membrane" means that the compact portion is not in contact with the surface of the membrane. The phrase "having the compact portion within the membrane" means that the compact portion is not the section closest to any surface of the membrane or that the compact portion is not a portion that contains the parting line closest to any surface of the membrane. In the membrane for immunoisolation of the embodiment of the present invention, by using the porous membrane having a structure having the compact portion within the membrane, permeability of a substance intended to permeate is unlikely to lower compared to a case of using a porous membrane having the same compact portion, which is in contact with the surface thereof. Although not bound by any theory, it is perceived that protein adsorption is less likely to occur due to the presence of the compact portion within the membrane.

It is preferable that the compact portion be biased to one of the front surface side than a central portion in thickness of the porous membrane. Specifically, the compact portion preferably located at a distance of less than half the thickness of the porous membrane from the surface of one of the porous membranes, more preferably located within a distance of two-fifths, even more preferably located within a distance of one-third, and particularly preferably located within a distance of one-fourth. This distance may be determined from the photograph of the membrane cross section described above. In the present specification, the surface of the porous membrane closer to the compact portion is referred to as a "surface X."

In the porous membrane, a pore diameter continuously increases in the thickness direction from the compact portion toward at least one of the surfaces. In the porous membrane, the pore diameter may continuously increase in the thickness direction toward the surface X from the compact portion, the pore diameter may continuously increase in the thickness direction toward the surface opposite to the surface X from the compact portion, and the pore diameter may continuously increase in the thickness direction toward any surface of the porous membrane from the compact portion. Among them, it is preferable that the pore diameter continuously increase in the thickness direction toward at least the surface opposite to the surface X from the compact portion, and it is preferable that the pore diameter continuously increase in the thickness direction toward any surface of the porous membrane from the compact portion. The sentence "the pore diameter continuously increases in the thickness direction" means that a difference in average pore diameters between sections or parting lines adjacent to each other in the thickness direction increases by 50% or less of a difference between maximum average pore diameters (maximum pore diameter) and minimum average pore diameters (minimum pore diameter), preferably by 40% or less, and more preferably by 30% or less. The phrase "continuously increasing" essentially means that a pore diameter increases uniformly without decreasing, but a decreasing portion may occur accidentally. For example, in a case of combining two sections from the surface, in a case where an average value of a combination increases uniformly (uniformly decreases toward the compact portion from the surface), it can be determined that "the pore diameter continuously increases in the thickness direction toward the surface of the membrane from the compact portion."

A structure of the porous membrane in which a pore diameter continuously increases in the thickness direction can be realized by, for example, a manufacturing method to be described later.

A maximum pore diameter of the porous membrane is preferably more than 1.5 µm and 25 µm or less, is more preferably 1.8 µm to 23 µm, and is even more preferably 2.0 µm to 21 µm. In the present specification, an average pore diameter of the section having a maximum average pore diameter among sections of the membrane cross section, or an average pore diameter of the parting line having the maximum average pore diameter among the parting lines, is used to refer to a maximum pore diameter of the porous membrane.

A ratio of an average pore diameter of the compact portion to the maximum pore diameter of the porous membrane (a ratio of a minimum pore diameter to a maximum pore diameter of the porous membrane, which is a value obtained by dividing the maximum pore diameter by the minimum pore diameter, an "anisotropy ratio" in the present specification) is preferably 3 or more, is more preferably 4 or more, and is even more preferably 5 or more. The reason is that an average pore diameter except for that of the compact portion increases to increase substance permeability of the porous membrane. In addition, the anisotropy ratio is preferably 25 or less, and is more preferably 20 or less. The reason is that effects, as though multistage filtration would be carried out, can be efficiently obtained within a range where an anisotropy ratio is 25 or less.

It is preferable that a section with a maximum average pore diameter be a section closest to any surface of the membrane or a section in contact with that section. In addition, it is preferable that a parting line where an average pore diameter becomes maximum be closest to any surface of the membrane.

In a diving or parting line closest to any surface of the membrane, it is preferable that an average pore diameter be more than 0.05 µm and 25 µm or less, be more preferably more than 0.08 µm and 23 µm or less, and be even more preferably more than 0.5 µm and 21 µm or less. In addition, a ratio of an average pore diameter of the compact portion to an average pore diameter of a diving or parting line closest to any surface of the membrane is preferably 1.2 to 20, is more preferably 1.5 to 15, and is even more preferably 2 to 13.

(Elemental Distribution of Porous Membrane)

Formulas (I) and (II) are preferably satisfied for at least one surface of the porous membrane.

$$B/A \leq 0.7 \tag{I}$$

$$A \geq 0.015 \tag{II}$$

In the formula, A represents a ratio of an N element (nitrogen atom) to a C element (carbon atom) on a surface of the membrane, and B represents a ratio of the N element to the C element at a depth of 30 nm from the same surface.

Formula (II) shows that a certain amount or more of N element is present on at least one surface of the porous membrane, and Formula (I) shows that an N element in the porous membrane is localized at a depth of less than 30 nm of the surface. An N element is preferably derived from a nitrogen-containing polymer. In addition, it is preferable that a nitrogen-containing polymer be polyvinylpyrrolidone.

With the surface satisfying Formulas (I) and (II), a bioaffinity of the porous membrane, particularly, a bioaffinity of the surface side satisfying Formulas (I) and (II) becomes high.

In the porous membrane, either one of surfaces may satisfy Formulas (I) and (II), or both surfaces may satisfy Formulas (I) and (II), but it is preferable that both surfaces satisfy Formulas (I) and (II). In a case where either one of surfaces satisfies Formulas (I) and (II), the surface thereof may be in an inside or an outside of a chamber for transplantation to be described later, but the surface is preferably in the inside thereof. In addition, in a case where only one of any surface satisfies Formulas (I) and (II), a surface satisfying Formulas (I) and (II) is preferably a surface X.

In the present specification, a ratio (A value) of N element to C element on the membrane surface and a ratio (B value) of N element to C element at a depth of 30 nm from the surface are obtained by calculating using XPS measurement results. The XPS measurement is X-ray photoelectron spectroscopy, which is a method for irradiating a membrane surface with X-rays, measuring kinetic energy of photoelectrons emitted from the membrane surface, and analyzing a composition of elements constituting the membrane surface. Under conditions using a monochromated Al-Kα ray described in Examples, the A value is calculated from results at the start of sputtering, and the B value is calculated from time results, which are calculated that the ray is at 30 nm from the surface of the membrane measured from a sputtering rate.

B/A may be 0.02 or more, is preferably 0.03 or more, and is more preferably 0.05 or more.

A is preferably 0.050 or more, and is more preferably 0.080 or more. In addition, A may be 0.20 or less, is preferably 0.15 or less, and is more preferably 0.10 or less.

B may be 0.001 to 0.10, is preferably 0.002 to 0.08, and is more preferably 0.003 to 0.07.

In a method for manufacturing the porous membrane which will be described later, the elemental distribution of the porous membrane, especially the distribution of an N element, can be controlled by a moisture concentration contained in the temperature-controlled humid air, a time to apply the temperature-controlled humid air, a temperature of a coagulation liquid, an immersion time, a temperature of a diethylene glycol bath for washing, an immersion time in the diethylene glycol bath for washing, a speed of a porous membrane manufacture line, and the like. The distribution of the N element can also be controlled by an amount of moisture contained in a stock solution for forming a membrane.

(Composition of Porous Membrane)

The porous membrane contains a polymer. It is preferable that the porous membrane be essentially composed of a polymer.

The polymer forming the porous membrane is preferably biocompatible. Here, the term "biocompatible" means that the polymer has non-toxic and non-allergenic properties, but does not have properties such that the polymer is encapsulated in a living body.

The number average molecular weight (Mn) of the polymer is preferably 1,000 to 10,000,000, and is more preferably 5,000 to 1,000,000.

Examples of polymers include thermoplastic or thermosetting polymers. Thermoplastic polymers are preferred. Specific examples of the polymer include polysulfone, cellulose acylate such as cellulose acetate, nitrocellulose, sulfonated polysulfone, polyethersulfone, polyvinylidene fluoride, polyacrylonitrile, styrene-acrylonitrile copolymer, styrene-butadiene copolymer, saponified ethylene-vinyl acetate copolymer, polyvinyl alcohol, polycarbonate, an organosiloxane-polycarbonate copolymer, a polyester carbonate, an organopolysiloxane, a polyphenylene oxide, a polyamide, a polyimide, polyamideimide, polybenzimidazole, ethylene vinyl alcohol copolymer, polytetrafluoroethylene (PTFE), and the like. From the viewpoints of solubility, optical physical properties, electrical physical properties, strength, elasticity, and the like, polymers may be homopolymers, copolymers, polymer blends, or polymer alloys.

Among them, polysulfone and cellulose acylate are preferable, and polysulfone is more preferable.

In a case where polysulfone or polyethersulfone is used as the polymer, the porous membrane preferably further contains a hydrophilic polymer. Preferable examples of hydrophilic polymers include polyvinylpyrrolidone, hydroxypropyl cellulose, and hydroxyethyl cellulose. Among them, polyvinylpyrrolidone is particularly preferable. By combining hydrophobic polysulfone or polyethersulfone with hydrophilic polyvinylpyrrolidone, biocompatibility can be improved. Polyvinylpyrrolidone is preferably contained by an amount of 0.05 to 8.0% by mass, more preferably 0.1 to 5.0% by mass, and even more preferably 0.2 to 4.0% by mass, with respect to a mass of the porous membrane.

The porous membrane may contain other components than the polymer as an additive.

Examples of additives include metal salts of inorganic acids such as sodium chloride, lithium chloride, sodium nitrate, potassium nitrate, sodium sulfate, and zinc chloride; metal salts of organic acids such as sodium acetate and sodium formate; other polymers such as polyethylene glycol; high polymer electrolytes such as sodium polystyrene sulfonate and polyvinyl benzyl trimethyl ammonium chloride; ionic surfactants such as sodium dioctyl sulfosuccinate and sodium alkyl sodium taurate; and the like. The additive may act as a swelling agent for a porous structure.

As an additive, it is preferable to use a metal salt. The porous membrane containing polysulfone or polyethersulfone preferably contains lithium chloride.

The porous membrane is preferably a membrane formed from a single composition as a single layer, and preferably not has a laminated structure of a plurality of layers. By forming the porous membrane from one composition as a single layer, it is possible to manufacture the membrane for immunoisolation at low costs by a simple procedure.

(Method for Manufacturing Porous Membrane)

A method for manufacturing the porous membrane is not particularly limited as long as the method can form the porous membrane having the above structure, and any general methods for forming a polymer membrane can be used. Examples of methods for forming a polymer membrane include a stretching method, a casting method, and the like, and a casting method is preferable.

For example, in the casting method, it is possible to produce a porous membrane having the above-mentioned structure by adjusting the type and amount of a solvent used in a stock solution for forming a membrane, and a drying method after casting.

Manufacture of a porous membrane by a casting method can be carried out by a method including, for example, the following (1) to (4) in this order.

(1) A stock solution for forming a membrane, which contains a polymer, if necessary an additive and, if necessary a solvent, is flow-cast on a support while being in a dissolved state.

(2) The surface of the flow-cast liquid membrane is exposed to temperature-controlled humid air.

(3) The membrane obtained after being exposed to temperature-controlled humid air is immersed in a coagulation liquid.

(4) A support is peeled off if necessary.

A temperature of temperature-controlled humid air may be 4° C. to 60° C., and is preferably 10° C. to 40° C. A relative humidity of the temperature-controlled humid air may be 15% to 100%, and is preferably 25% to 95%. The temperature-controlled humid air may be applied at a wind speed of 0.1 m/s to 10 m/s for 0.1 seconds to 30 seconds, preferably 1 second to 10 seconds.

In addition, an average pore diameter and position of the compact portion can also be controlled by a moisture concentration contained in the temperature-controlled humid air and a time of applying the temperature-controlled humid air. An average pore diameter of the compact portion can also be controlled by an amount of moisture contained in a stock solution for forming a membrane.

By applying the temperature-controlled humid air to the surface of the liquid membrane as described above, it is possible to cause coacervation from the surface of the liquid membrane toward the inside of the membrane by controlling evaporation of a solvent. By immersing the membrane in a coagulation liquid containing a solvent having low solubility of the polymer but compatible with the solvent of the polymer in this state, the above-mentioned coacervation phase is fixed as fine pores, and pores other than the fine pores can also be formed.

A temperature of the coagulation liquid may be −10° C. to 80° C. in a process of immersing the membrane in the coagulation liquid. By changing a temperature during this period, it is possible to control a size of a pore diameter up to a support surface side by adjusting a time from the formation of the coacervation phase on the support surface side to the solidification from the compact portion. In a case where a temperature of the coagulation liquid is raised, the formation of the coacervation phase becomes faster and a time for solidification becomes longer, and therefore the pore diameter toward the support surface side tends to become large. On the other hand, in a case where a temperature of the coagulation liquid is lowered, the formation of the coacervation phase becomes slower and a time for solidification becomes shorter, and therefore the pore diameter toward the support surface side is unlikely to become large.

As the support, a plastic film or a glass plate may be used. Examples of materials of the plastic film include polyester such as polyethylene terephthalate (PET), polycarbonate, acrylic resin, epoxy resin, polyurethane, polyamide, polyolefin, a cellulose derivative, silicone, and the like. As the support, a glass plate or PET is preferable, and PET is more preferable.

The stock solution for forming a membrane may contain a solvent. A solvent having high solubility of the polymer to be used (hereinafter referred to as "favorable solvent") may be used depending on a polymer to be used. As a favorable solvent, it is preferable that the solvent be quickly substituted with the coagulation liquid in a case where the membrane is immersed in the coagulation liquid. Examples of solvents include N-methyl-2-pyrrolidone, dioxane, tetrahydrofuran, dimethylformamide, dimethylacetamide, or a mixed solvent thereof in a case where the polymer is polysulfone and the like; dioxane, N-methyl-2-pyrrolidone, dimethylformamide, dimethylacetamide, dimethylsulfoxide, or a mixed solvent thereof in a case where the polymer is polyacrylonitrile and the like; dimethylformamide, dimethylacetamide, or a mixed solvent thereof in a case where the polymer is polyamide and the like; acetone, dioxane, tetrahydrofuran, N-methyl-2-pyrrolidone, or a mixed solvent thereof in a case where the polymer is cellulose acetate and the like. Among them, N-methyl-2-pyrrolidone is preferably used.

In addition to a favorable solvent, the stock solution for forming a membrane preferably use a solvent (hereinafter referred to as "non-solvent") in which the solubility of the polymer is low but is compatible with the solvent of the polymer. Examples of non-solvents include water, cellosolves, methanol, ethanol, propanol, acetone, tetrahydrofuran, polyethylene glycol, glycerin, and the like. Among these, it is preferable to use water.

A concentration of the polymer as the stock solution for forming a membrane may be 5% by mass to 35% by mass, is preferably 10% by mass to 30% by mass. By setting the concentration thereof to 35 mass % or less, sufficient permeability (for example, water permeability) can be imparted to the obtained porous membrane. By setting the concentration thereof to 5 mass % or more, the formation of a porous membrane which selectively allows substances to permeate can be secured. An amount of additive to be added is not particularly limited as long as the homogeneity of the stock solution for forming a membrane is not lost by the addition, but is 0.5% by volume to 10% by volume respect to a general solvent. In a case where the stock solution for forming a membrane contains a non-solvent and a favorable solvent, a ratio of the non-solvent to the favorable solvent is not particularly limited as long as a mixed solution can be maintained in a homogeneous state, but is preferably 1.0% by mass to 50% by mass, is more preferably 2.0% by mass to 30% by mass, and is even more preferably 3.0% by mass to 10% by mass.

In addition, in the stock solution for forming a membrane for manufacturing a porous membrane containing a polymer selected from the group consisting of polysulfone and polyethersulfone, and containing polyvinylpyrrolidone, polyvinylpyrrolidone is preferably contained by an amount of 50% by mass to 120% by mass, and more preferably by an amount of 80% by mass to 110% by mass, with respect to a total mass of polysulfone and polyethersulfone. By using such a stock solution for forming a membrane, a porous membrane containing about 0.05% to 8.0 mass % of polyvinylpyrrolidone is obtained. The reason why an amount of polyvinylpyrrolidone is reduced is that most parts of polyvinylpyrrolidone are removed in a washing step.

Furthermore, in a case where the stock solution for forming a membrane contains lithium chloride as an additive, lithium chloride is preferably contained by an amount of 5% by mass to 20% by mass, and more preferably by 10% by mass to 15% by mass, with respect to the total mass of polysulfone and polyethersulfone.

As the coagulation liquid, it is preferable to use a solvent having a low solubility of the polymer used. Examples of such solvents include water, alcohols such as methanol, ethanol, and butanol; glycols such as ethylene glycol and diethylene glycol; aliphatic hydrocarbons such as ether, n-hexane, and n-heptan; glycerol such as glycerin; and the like. Examples of preferred coagulation liquids include water, alcohols, or a mixture of two or more of these. Among these, it is preferable to use water.

After immersion in the coagulation liquid, it is also preferable to perform washing with a solvent different from the coagulation liquid that has been used. Washing can be carried out by immersing in a solvent. Diethylene glycol is preferable as a washing solvent. Distribution of an N element in the porous membrane can be adjusted by adjusting either or both of a temperature and an immersion time of diethylene glycol in which a film is immersed by using diethylene glycol as a washing solvent. In particular, in a case where polyvinylpyrrolidone is used as the stock solution for forming a membrane of the porous membrane, a residual amount of polyvinylpyrrolidone on the membrane can be controlled. After washing with diethylene glycol, furthermore, the membrane may be washed with water.

As the stock solution for forming a membrane of the porous membrane, the stock solution for forming a membrane, which is obtained by dissolving polysulfone and polyvinylpyrrolidone in N-methyl-2-pyrrolidone and adding water, is preferable.

Regarding a method for manufacturing the porous membrane, reference can be made to JP1992-349927A (JP-H04-349927A), JP1992-068966B (JP-H04-068966B), JP1992-351645A (JP-H04-351645A), JP2010-235808A, and the like.

[Other Layers]

The membrane for immunoisolation of the embodiment of the present invention may contain layers other than the porous membrane. Examples of other layers include a hydrogel membrane. As a hydrogel membrane, a biocompatible hydrogel membrane is preferable. Examples thereof include an alginic acid gel membrane, an agarose gel membrane, a polyisopropyl acrylamide membrane, a membrane containing cellulose, a membrane containing a cellulose derivative (for example, methyl cellulose), a polyvinyl alcohol membrane, or the like. The hydrogel membrane is preferably an alginic acid gel membrane. Specific examples of alginic acid gel membranes include a polyion complex membrane of alginic acid-poly-L-lysine-alginic acid.

<Use of Membrane for Immunoisolation>

The membrane for immunoisolation can be used to prevent an immune rejection. Specifically, the membrane for immunoisolation can be used to prevent an immune rejection by a recipient with respect to a transplanted biological constituent. That is, the membrane for immunoisolation can be used for protecting biological constituents from an immune system of a recipient. In the present specification, a recipient means a living body to which transplantation is performed. A recipient is preferably a mammal, and is more preferably a human.

[Biological Constituent]

The biological constituent means a structure body derived from a living body. Examples of living bodies include viruses, bacteria, yeasts, fungal cells, insects, plants, mammals, and the like. It is preferable that a living body be generally a mammal. Examples of mammals include bovines, swine, sheep, cats, dogs, humans, and the like. The biological constituent is preferably a structure body derived from any of mammals.

Examples of biological constituents include organs, tissues, cells, and the like. Among these, cells are preferred as biological constituents. As cells, a single cell may be used or a plurality of cells may be used. It is preferable that a plurality of cells be used. A plurality of cells may be separated from each other or may be an aggregate.

The biological constituent may be obtained directly from a living body. In addition, particularly in a case where the biological constituent is a cell, the biological constituent may be directly obtained from a living body, or may be obtained by differentiation-induction of cells such as embryonic stem cells (ES cell), induced pluripotent stem cells (iPS cell), and mesenchymal stem cells. The cell may be a progenitor cell.

As a biological constituent, as one aspect, it is preferable to release a physiologically active substance. Examples of physiologically active substances include various hormones, various cytokines, various enzymes, and various other biologic factors in a living body. More specific examples include insulin, dopamine, factor VIII, and the like.

Here, insulin is a polypeptide (molecular weight of about 6000) in which an A chain of 21 amino acid residues and a B chain of 30 amino acid residues are linked via a disulfide bond. In insulin in a living body of a mammal is secreted from β cells in pancreatic islets of Langerhans. In a case of using insulin-secreting cells as the biological constituent in the present invention, insulin secreted may be human-type insulin or other mammalian-type (for example, porcine-type) insulin. Insulin may be insulin produced by a genetic recombination method. As a method for obtaining genetically modified insulin, for example, the description of Kadowaki Takashita: Diabetes Navigator (refer to 270-271, Takeo Tao, Yoshikazu Oka "Insulin Preparations of Present and Future," Medical Review, 2002) can be referred to. Various types of insulin analogues (refer to, for example, H. C. Lee, J. W. Yoon, et al., Nature, 408, 483-488, 2000) may be used.

The biological constituent is preferably an insulin-secreting cell. Insulin-secreting cells are cells that can secrete insulin in response to changes in blood glucose level. The insulin-secreting cells are not particularly limited. Examples thereof include pancreatic β cells present in pancreatic islets of Langerhans. Pancreatic β cells may be human pancreatic β cells, or may be pancreatic β cells such as pigs and mice. For a method for extracting pancreatic β cells from a pig, reference can be made to the description in JP2007-195573A. In addition, the insulin-secreting cells may be cells derived from human stem cells (refer to, for example, Junichi Miyazaki, Regenerative Medicine, Vol. 1, No. 2, pp. 57-61, 2002), or cells induced from small intestinal epithelial stem cells (refer to, for example, Fumikomi Mineko et al., Regenerative Medicine, Volume 1, No. 2, pp. 63 to 68, 2002), or insulin-secretory cells into which a gene encoding insulin has been incorporated (refer to, for example, H. C. Lee, J. W. Yoon, et al., Nature, 408, pp. 483-488, 2000). Furthermore, the insulin-secreting cells may be pancreatic islets of Langerhans (refer to, for example, Horiyama, Kazumori Inoue, Regenerative Medicine, Volume 1, No. 2, pp. 69 to 77, 2002).

[Chamber for Transplantation]

The membrane for immunoisolation of the embodiment of the present invention can be used as a constructional element of a chamber for transplantation for enclosing the biological constituent therein. The chamber for transplantation can be used as a container for enclosing the biological constituent in a case of transplanting the biological constituent into a recipient. The membrane for immunoisolation is disposed on at least a part of the surface forming the inside and the outside of the chamber for transplantation (a boundary that separates the inside and the outside of the chamber for transplantation). By disposing in such a manner, it is possible to protect the biological constituent enclosed in the chamber for transplantation from immune cells and the like present outside, and to introduce nutrients such as water, oxygen, and glucose into the inside of the chamber for transplantation from the outside.

The membrane for immunoisolation may be disposed on the entire surface forming the inside and the outside of the chamber for transplantation, and may be disposed a part of the surface corresponding to an area of, for example, 1% to 99%, 5% to 90%, 10% to 80%, 20% to 70%, 30% to 60%, 40% to 50%, or the like with respect to the entire area. A surface on which the membrane for immunoisolation is disposed may be one continuous portion or may be divided into two or more portions. In a case where the membrane for immunoisolation is not disposed on the entire surface of the boundary forming the inside and the outside of the chamber for transplantation, it is sufficient that remaining portions are formed of a material such as an impermeable membrane not allowing permeation of nutrients such as oxygen, water, and glucose, in addition to cells and the like.

A shape of the chamber for transplantation is not limited, and may be a pouched-like shape, a bag shape, a tube shape, a microcapsule shape, or a drum shape. For example, a drum-shaped chamber for transplantation can be formed by adhering the membrane for immunoisolation to the top and bottom of a silicone ring. A shape of the chamber for transplantation is preferably a shape capable of preventing movement of the chamber for transplantation within a recipient in a case where the chamber for transplantation is used as a device for transplantation to be described later. Specific examples of shapes of the chamber for transplantation include a cylindrical shape, a disk-like shape, a rectangular shape, an egg shape, a star shape, a circular shape, and the like. The chamber for transplantation may be in a form of a sheet, a strand, a spiral, or the like. The chamber for transplantation may be a chamber for transplantation which encloses the biological constituent and becomes the above-described shape only in a case where the chamber for transplantation used as a device for transplantation to be described later.

The chamber for transplantation may contain a biocompatible plastic or the like for maintaining the shape and strength as a container. For example, the boundary between the inside and the outside of the chamber for transplantation may be made from the membrane for immunoisolation and a biocompatible plastic that does not correspond to the membrane for immunoisolation. In addition, in the chamber for transplantation in which the membrane for immunoisolation is disposed on the entire surface forming substantially the inside and the outside, a biocompatible plastic having a net-like structure may be further disposed on the outside of the surface forming the inside and the outside, from the viewpoint of strength.

In the chamber for transplantation, it is preferable that the surface X of the porous membrane be on the inside thereof. That is, it is preferable that the membrane for immunoisolation be disposed so that the compact portion of the porous membrane in the membrane for immunoisolation is closer to the inside of the chamber for transplantation. By setting the surface X in the inside of the chamber for transplantation, it is possible to make permeability of physiologically active substances higher.

The chamber for transplantation may have a joint portion at which the membranes for immunoisolation face each other to be joined. A portion of the membrane for immunoisolation that is being joined is not particularly limited, but is preferably an end portion of the membrane for immunoisolation. In particular, it is preferable that end portions be joined to each other. It is preferable that all of outer peripheries except an injection port and the like to be described later be joined to each other between the membranes for immunoisolation. For example, the chamber for transplantation preferably has a configuration in which two membranes for immunoisolation face each other and outer peripheries thereof are joined, or a structure in which one membrane for immunoisolation having a line symmetric structure is folded into two and facing outer peripheries are joined. Joining can be performed by adhesion using an adhesive, fusion welding, and the like.

In addition, the chamber for transplantation may include an injection port or the like for injecting the biological constituent or the like into the chamber for transplantation. As the injection port, a tube communicating with the inside of the chamber for transplantation may be provided.

The tube may be a tube containing a thermoplastic resin such as polyethylene, polyurethane, or polyvinyl chloride.

In addition, the chamber for transplantation may have a structure-reinforcing material which is for protecting internal biological constituents and the like. The structure-reinforcing material may be provided inside or outside the chamber for transplantation.

The structure-reinforcing material may be mesh, nets, nonwoven fabrics, woven fabrics, metals, resins, or the like.

[Device for Transplantation]

The device for transplantation is a complex including at least the chamber for transplantation and the biological constituent. In the device for transplantation, the chamber for transplantation encloses the biological constituent therein.

In the device for transplantation, the chamber for transplantation may enclose only the biological constituent therein, or may enclose the biological constituent, and constituents or components other than the biological constituent therein. For example, the biological constituent may be enclosed in the chamber for transplantation together with a hydrogel, and preferably in a state of being enclosed in the hydrogel. In addition, the device for transplantation may contain pH buffers, inorganic salts, organic solvents, proteins such as albumin, or peptides.

The device for transplantation may contain only one biological constituent or may contain two or more biological constituents. For example, the device for transplantation may contain only a biological constituent which releases physiologically active substances for the purpose of transplantation, or which serves other functions of transplantation; or may further contain a biological constituent assisting functions of these biological constituents.

The device for transplantation may be, for example, a device to be transplanted intraperitoneally or subcutaneously. In addition, the device for transplantation may be a blood-vessel-connecting device. For example, in a case where insulin-secreting cells are used as the biological constituent, insulin secretion corresponding to a change in blood glucose level becomes possible by performing transplantation such that blood and the membrane for immunoisolation come into direct contact with each other.

Regarding the device for transplantation and chamber for transplantation, the description of Protein Nucleic Acid Enzyme, Vol. 45, pp. 2307 to 2312, (Okawara Hisako, 2000), JP2009-522269A, JP1994-507412A (JP-H06-507412A), and the like can be referred to.

EXAMPLES

Characteristics of the present invention will be described in more detail with reference to the following examples and comparative examples. The materials, amounts used, proportions, treatment details, treatment procedures, and the like disclosed in the following Examples can be modified as appropriate as long as the gist of the invention is maintained. Therefore, the scope of the invention should not be limitedly interpreted by the specific examples described below.

<Production of Porous Membrane>
[Porous Membranes 1 to 13]

15 parts by mass of polysulfone (P3500 manufactured by Solvay), 15 parts by mass of polyvinylpyrrolidone, 2 parts by mass of lithium chloride, and 1.2 parts by mass of water were dissolved in 66.8 parts by mass of N-methyl-2-pyrrolidone. Therefore, a mixture for forming a membrane was obtained. This mixture was flow-cast on a surface of a PET film by a thickness of 200 µm. The flow-cast membrane surface was exposed to air adjusted to 25° C. and absolute humidity 7.8 g/kg air, at 2 m/sec for 5 seconds. Immediately thereafter, the exposed membrane surface was immersed in a coagulation liquid tank filled with water. PET was peeled off, and therefore a porous membrane was obtained. Thereafter, at 2 m/sec, the immersed membrane surface was put into a diethylene glycol bath at 25° C. for 120 seconds, and then was thoroughly washed with pure water.

An amount of moisture (0.1 to 1.4 parts by mass) in the stock solution, and an absolute humidity (6.1 to 10.0 g/kg air) of humidity conditioned air after casting were adjusted. Therefore, porous membranes 1 to 9 of which a pore diameter of the compact portion is a value shown in Table 1 were obtained. Furthermore, a temperature of the coagulation bath was adjusted from −10° C. to 80° C., and therefore porous membranes 10 to 13 were obtained. A thickness of each membrane after drying was 195 to 205 µm.

[Porous Membrane 110]

A side, where a pore diameter is larger, of a polysulfone membrane (T9EXPPA1000S00M, manufactured by Nippon Pall Co., Ltd., thickness of 130 µm) having a pore diameter of 10 µm was laminated to a side, where a pore diameter is small, of a polysulfone membrane (T9EXPPA0080S00B, manufactured by Nippon Pall Co., Ltd., thickness of 120 µm) having pore diameter distribution in which a pore diameter continuously increases in the thickness direction, and having the minimum pore diameter (0.8 µm) on an outermost surface. Therefore, a porous membrane 110 was obtained. In the porous membrane 110, the polysulfone membrane side having the minimum pore diameter of 0.8 µm is defined as the surface X (refer to Table 1).

[Porous Membrane 120]

A polysulfone membrane (T9EXPPA0080S00B, thickness of 130 µm) having pore diameter distribution in which a pore diameter continuously increases in the thickness direction, and having the minimum pore diameter (0.8 µm) on an outermost surface was prepared. Therefore, a porous membrane 120 was obtained. In the porous membrane 120, the surface side having the minimum pore diameter is defined as the surface X (refer to Table 1).

[Porous Membrane 130]

A side, where a pore diameter is larger, of a polysulfone membrane (T9EXPPA1000S00M, manufactured by Nippon Pall Co., Ltd., thickness of 130 µm) having a pore diameter of 10 µm was laminated to a side, where a pore diameter is large, of a polysulfone membrane (T9EXPPA0080S00B, manufactured by Nippon Pall Co., Ltd.) having pore diameter distribution in which a pore diameter continuously increases in the thickness direction, and having the minimum pore diameter (0.8 µm) on an outermost surface. Therefore, a porous membrane 130 was obtained. In the porous membrane 130, the polysulfone membrane side having the minimum pore diameter of 0.8 µm is defined as the surface X (refer to Table 1).

<Structure Analysis of Porous Membrane>

Figure 2:
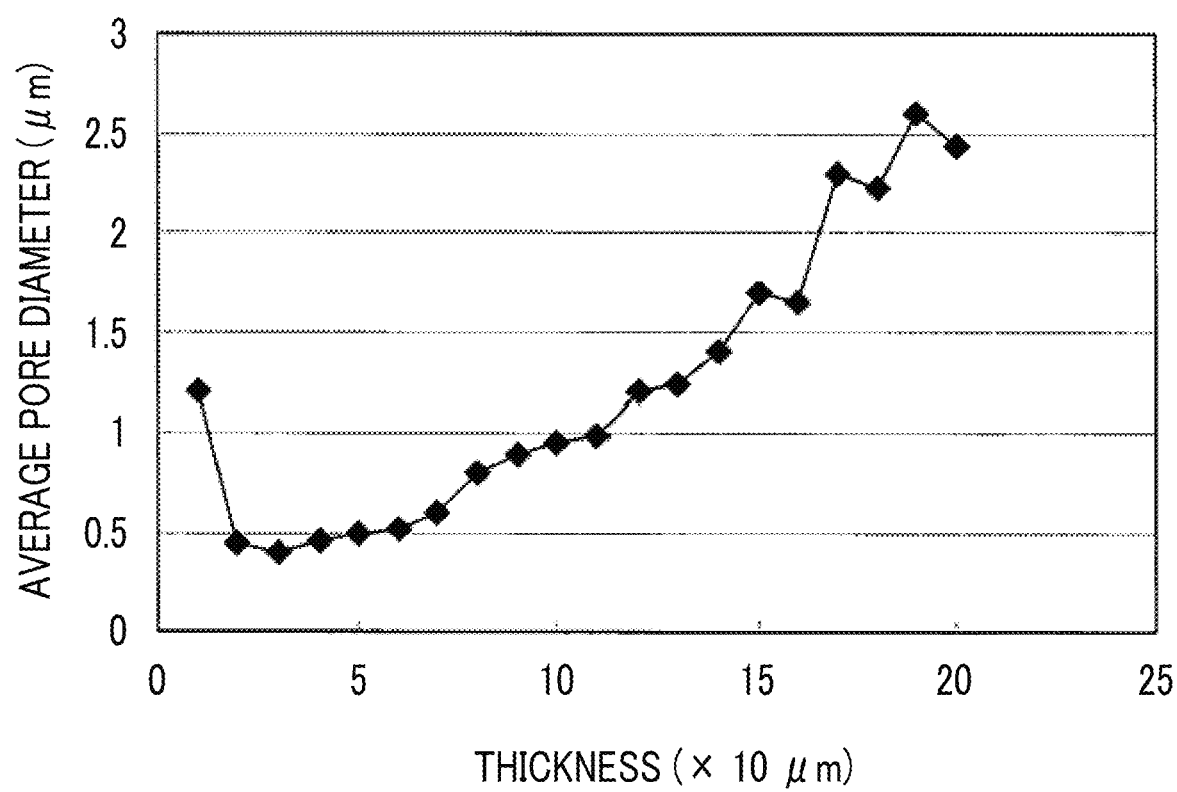
FIG. 2 is a graph showing distribution of an average pore diameter in a thickness direction of the porous membrane 3 (membrane for immunoisolation) obtained in Examples.

Each porous membrane obtained was impregnated with methanol and frozen in liquid nitrogen. Sections for cross section observation were cut out from the frozen porous membrane with a microtome (EM UC6 manufactured by Leica), and subjected to SEM imaging (SU8030 type FE-SEM manufactured by Hitachi High-Technologies Corporation). SEM imaging was performed at 3000 times. A photograph of a cross section of the porous membrane 3 is shown in FIG. 1. In FIG. 1, an upper side is a side exposed to air at the time of manufacture, and a lower side is a PET film side at the time of manufacture. An SEM image photograph of a cross section of each porous membrane was divided into 20 in the thickness direction from the upper side, pores of each obtained section were traced with a digitizer, and therefore an average pore diameter of 50 pores in each section was obtained. However, for a section in which pores were large and therefore only less than 50 pores could be measured, only available number of pores that could be counted in that section was measured. The obtained average pore diameter of each section was plotted in order from one surface to the other surface, and therefore distribution of the average pore diameter in the thickness direction of the membrane was obtained. Measurement results of the porous membrane 3 are shown in FIG. 2. A section having the smallest average pore diameter was used as a compact portion, and the average pore diameter of this portion was measured by a separate ASTM F316-80 method. In addition, an average pore diameter of the section where an average pore diameter becomes maximum was obtained as a maximum pore diameter. Measured values are shown in Table 1.

<Evaluation of Porous Membrane>

(Insulin Permeability)

A hole having a diameter of 1.0 cm was made in the center of one wall surface of a container made from vinyl chloride which has a size of 2.0 cm in length, 1.0 cm in width, and 2.0 cm in height, and the periphery of the hole was covered with a silicone sheet (50°, thickness of 1 mm) made from Tigers polymer. A porous membrane cut into 1.5 cm×2.0 cm was placed so as to cover the silicone sheet. Other same container and a silicone sheet were prepared and fixed with a clip such that the holes were aligned. A fixed porous membrane was often infiltrated with a medium (medium for pancreatic islet culture, Cosmobio, PNIM3).

4.0 mL of a medium (medium for pancreatic islet culture, Cosmobio, PNIM3) containing 0.1 unit of insulin (Wako Pure Chemical Industries, Ltd., Insulin Humane Recombinant, 097-06474) was put into one container (supply side). 4.0 mL of the same medium but not containing insulin was put into the other container (permeation side). A surface X of the porous membrane was set to either the supply side or the permeation side as shown in Table 1. After 240 minutes, the media on the supply side and permeation side were collected. An amount of insulin was quantitatively determined with Insulin ELISA (80-INSRT-E01 manufactured by ALPCO), and evaluated according to the following criteria. The results are shown in Table 1.

An insulin concentration on the permeation side was 95% or more compared to the supply side after 240 minutes: AA An insulin concentration on the permeation side was 70% or more compared to the supply side after 240 minutes: A An insulin concentration on the permeation side was 45% or more compared to the supply side after 240 minutes: B An insulin concentration on the permeation side was less than 45% compared to the supply side after 240 minutes: C (Cell Infiltration Inhibitory)

Inhibition of cell infiltration into the inside of the membrane in a living body was evaluated on the porous membrane produced above, as follows. Evaluation of cell infiltration inhibitory is an indicator of a function of blocking various cells.

Figure 3:
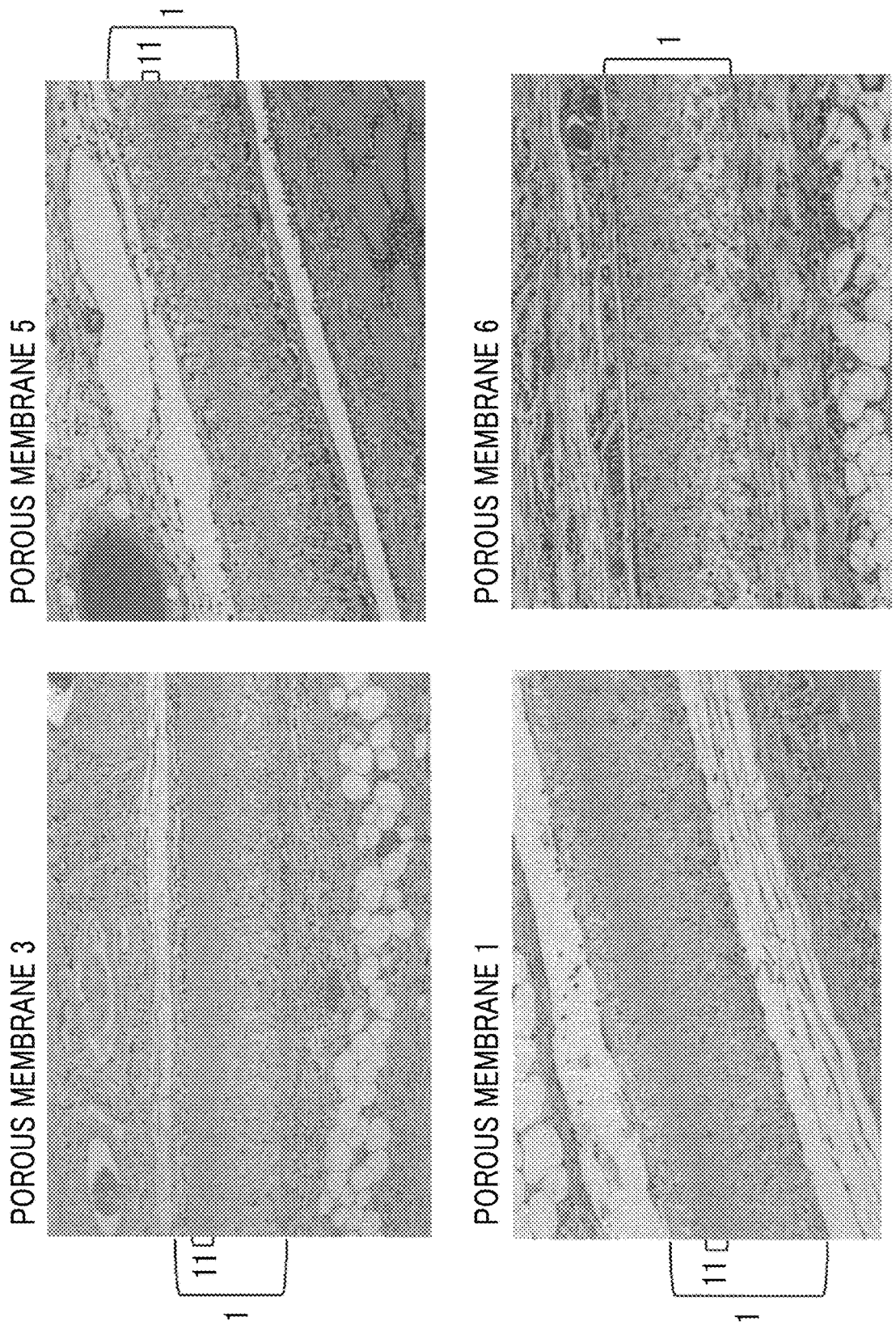
FIG. 3 shows images of histologically stained sections containing porous membranes 1, 3, 5, and 6 obtained in Examples.

A 2 cm square porous membrane was implanted subcutaneously at the back of an SD rat (Sprague-Dawley rat) and sutured. After breeding for 1 week, the same portion was excised. Sections histologically stained with hematoxylin/eosin (HE) were produced. An image of a cross section of the portion where the porous membrane was implanted was captured. FIG. 3 shows images of histologically stained sections containing the porous membranes 1, 3, 5, and 6. As can be seen from FIG. 3, in the porous membranes 1, 3, and 5, a cell-infiltration-inhibiting layer was observed, thereby inhibiting cell infiltration. On the other hand, in the porous membrane 6, a cell-infiltration-inhibiting layer was observed, but a section where cells were infiltrated was observed in some part. Therefore, it can be determined that a level of cell infiltration inhibitory is moderate. Each porous membrane was evaluated according to the following criteria.

A: A cell-infiltration-inhibiting layer was observed.

B: A cell-infiltration-inhibiting layer was observed, but a section where cells were infiltrated was observed in some part.

C: No clear cell-infiltration-inhibiting layer was observed, and cells were infiltrated throughout.

The results are shown in Table 1.

(Membrane Durability)

In a sterile state, the porous membrane was immersed in a medium (medium for pancreatic islet culture, Cosmobio, PNIM3) and stored at 37° C. for 1 month. Thereafter, insulin permeability was tested in the same manner as described above.

The results are shown in Table 1.

TABLE 1

|  | Example 1 | Comparative Example 1 | Comparative Example 2 | Comparative Example 3 | Example 2 | Example 3 |
|---|---|---|---|---|---|---|
| Porous membrane | 1 | 110 | 120 | 130 | 2 | 3 |
| Location of compact portion | Inside | | Surface | | Inside | |
| Consecutiveness of pore diameter | Consecutive | Inconsecutive | Consecutive | Inconsecutive | Consecutive | Consecutive |
| Minimum pore diameter (μm) | 0.8 | 0.8 | 0.8 | 0.8 | 0.2 | 0.45 |
| Maximum pore diameter (μm) | 5.6 | — | — | — | 2.0 | 2.6 |
| Anisotropy ratio | 7.0 | — | — | — | 10.0 | 5.8 |
| Direction of surface X | Supply side | Supply side | Supply side | Supply side | Supply side | Supply side |
| Insulin permeability | AA | B | B | B | A | AA |
| Cell infiltration inhibitory | A | A | C | A | A | A |
| Membrane durability | A | C | B | C | A | A |

|  | Example 4 | Example 6 | Example 7 | Example 8 | Example 9 | Example 10 |
|---|---|---|---|---|---|---|
| Porous membrane | 4 | 5 | 6 | 7 | 8 | 9 |
| Location of compact portion | | | Inside | | | |
| Consecutiveness of pore diameter | Consecutive | Consecutive | Consecutive | Consecutive | Consecutive | Consecutive |
| Minimum pore diameter (μm) | 0.6 | 1.2 | 1.4 | 0.01 | 0.02 | 0.08 |
| Maximum pore diameter (μm) | 3.4 | 15.0 | 21.0 | 0.07 | 0.14 | 0.50 |
| Anisotropy ratio | 5.7 | 12.5 | 15.0 | 7.0 | 7.0 | 6.3 |
| Direction of surface X | Supply side | Supply side | Supply side | Supply side | Supply side | Supply side |
| Insulin permeability | AA | AA | AA | B | A | A |
| Cell infiltration inhibitory | A | A | B | A | A | A |
| Membrane durability | A | A | A | A | A | A |

|  | Example 11 | Example 12 | Example 13 | Example 14 | Example 16 | Example 17 |
|---|---|---|---|---|---|---|
| Porous membrane | 1 | 2 | 3 | 4 | 5 | 6 |
| Location of compact portion | | | Inside | | | |
| Consecutiveness of pore diameter | Consecutive | Consecutive | Consecutive | Consecutive | Consecutive | Consecutive |
| Minimum pore diameter (μm) | 0.8 | 0.2 | 0.45 | 0.6 | 1.2 | 1.4 |
| Maximum pore diameter (μm) | 5.6 | 2.0 | 2.6 | 3.4 | 15.0 | 21.0 |
| Anisotropy ratio | 7.0 | 10.0 | 5.8 | 5.7 | 12.5 | 15.0 |
| Direction of surface X | Permeation side | Permeation side | Permeation side | Permeation side | Permeation side | Permeation side |

TABLE 1-continued

|  | | | | | | | |
|---|---|---|---|---|---|---|---|
| Insulin permeability | AA | A | A | AA | AA | AA |  |
| Cell infiltration inhibitory | A | A | A | A | A | B |  |
| Membrane durability | A | A | A | A | A | A |  |

|  | Example 18 | Example 19 | Example 20 | Example 21 | Example 22 | Example 23 | Example 24 |
|---|---|---|---|---|---|---|---|
| Porous membrane | 7 | 8 | 9 | 10 | 11 | 12 | 13 |
| Location of compact portion |  | Inside | | | | Inside | |
| Consecutiveness of pore diameter | Consecutive | Consecutive | Consecutive | Consecutive | Consecutive | Consecutive | Consecutive |
| Minimum pore diameter (μm) | 0.01 | 0.02 | 0.08 | 0.8 | 0.8 | 0.8 | 0.8 |
| Maximum pore diameter (μm) | 0.07 | 0.08 | 0.50 | 2.2 | 2.5 | 15.0 | 18.0 |
| Anisotropy ratio | 7.0 | 4.0 | 6.3 | 2.8 | 3.1 | 18.8 | 22.5 |
| Direction of surface X | Permeation side | Permeation side | Permeation side | Permeation side | Permeation side | Permeation side | Permeation side |
| Insulin permeability | B | B | A | AA | AA | AA | AA |
| Cell infiltration inhibitory | A | A | A | A | A | A | A |
| Membrane durability | A | A | A | B | A | A | B |

Example 25

15 parts by mass of polysulfone (P3500 manufactured by Solvay), 15 parts by mass of polyvinylpyrrolidone (K-30 manufactured by Nippon Shokubai Co., Ltd.), 1 part by mass of lithium chloride, and 2 parts by mass of water were dissolved in 67 parts by mass of N-methyl-2-pyrrolidone. Therefore, a stock solution for forming a membrane was obtained. This stock solution for forming a membrane was flow-cast on a surface of polyethylene terephthalate (PET) film with a wet thickness such that a dry thickness became 50 μm. The flow-cast membrane surface was exposed to air adjusted to 30° C. and relative humidity 80% RH, at 2 msec for 5 seconds. Immediately thereafter, the exposed membrane surface was immersed in a coagulation liquid tank at 65° C. filled with water. The PET film was peeled off, and therefore a porous membrane was obtained. Thereafter, the immersed membrane surface was put into a diethylene glycol bath at 80° C. for 120 seconds, and then was thoroughly washed with pure water. Therefore, a porous membrane having a dry thickness of 50 μm was obtained. This was used as a porous membrane 14.

Example 26

15 parts by mass of polysulfone (P3500 manufactured by Solvay), 15 parts by mass of polyvinylpyrrolidone (K-30 manufactured by Nippon Shokubai Co., Ltd.), 1 part by mass of lithium chloride, and 2 parts by mass of water were dissolved in 67 parts by mass of N-methyl-2-pyrrolidone. Therefore, a stock solution for forming a membrane was obtained. This stock solution for forming a membrane was flow-cast on a surface of a PET film with a wet thickness such that a dry thickness became 83 The flow-cast membrane surface was exposed to air adjusted to 30° C. and relative humidity 57% RH, at 2 m/sec for 5 seconds. Immediately thereafter, the exposed membrane surface was immersed in a coagulation liquid tank at 70° C. filled with water. The PET film was peeled off, and therefore a porous membrane was obtained. Thereafter, the immersed membrane surface was put into a diethylene glycol bath at 80° C. for 120 seconds, and then was thoroughly washed with pure water. Therefore, a porous membrane having a dry thickness of 83 μm was obtained. This was used as a porous membrane 15.

<Structure Analysis of Porous Membranes 14 and 15>

Figure 4:
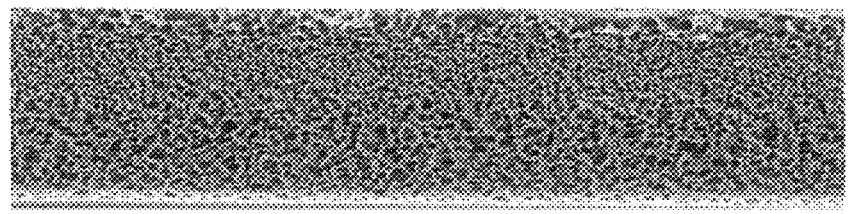
FIG. 4 is a view showing an SEM image of a cross section of a porous membrane 14 (membrane for immunoisolation) obtained in Examples.
Figure 5:
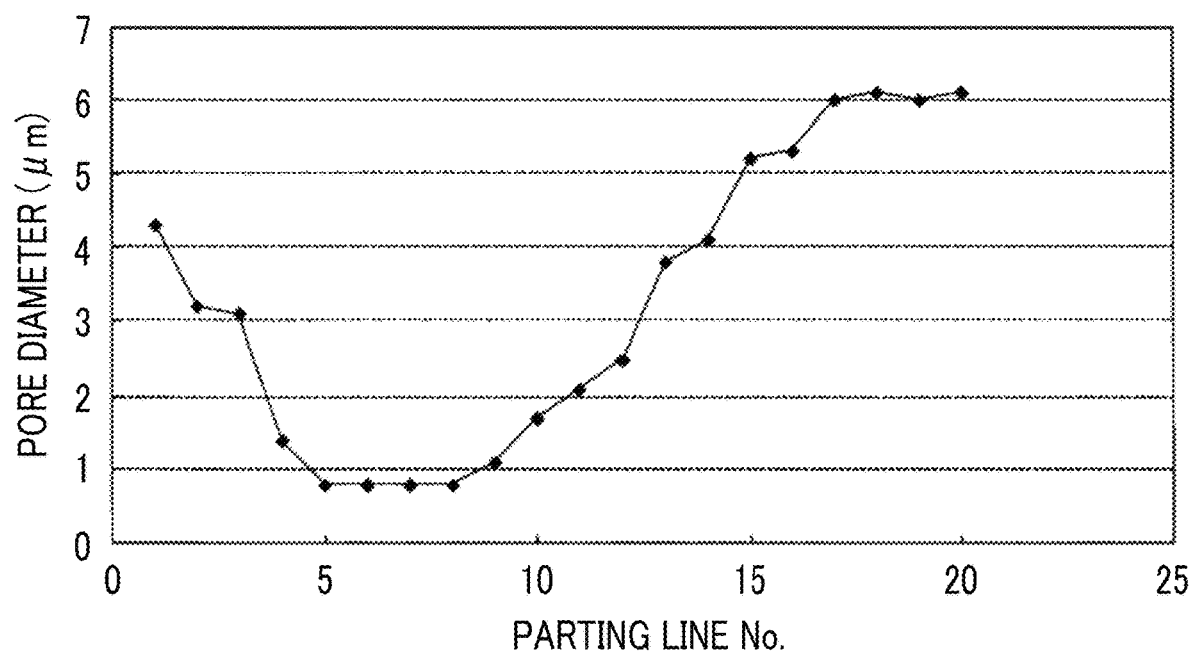
FIG. 5 is a graph showing distribution of an average pore diameter in a thickness direction of the porous membrane 14 (membrane for immunoisolation) obtained in Examples.
Figure 7:
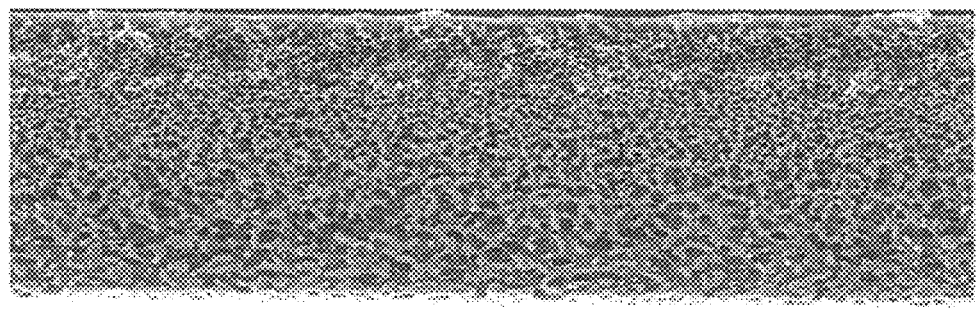
FIG. 7 is a view showing an SEM image of a cross section of a porous membrane 15 (membrane for immunoisolation) obtained in Examples.
Figure 8:
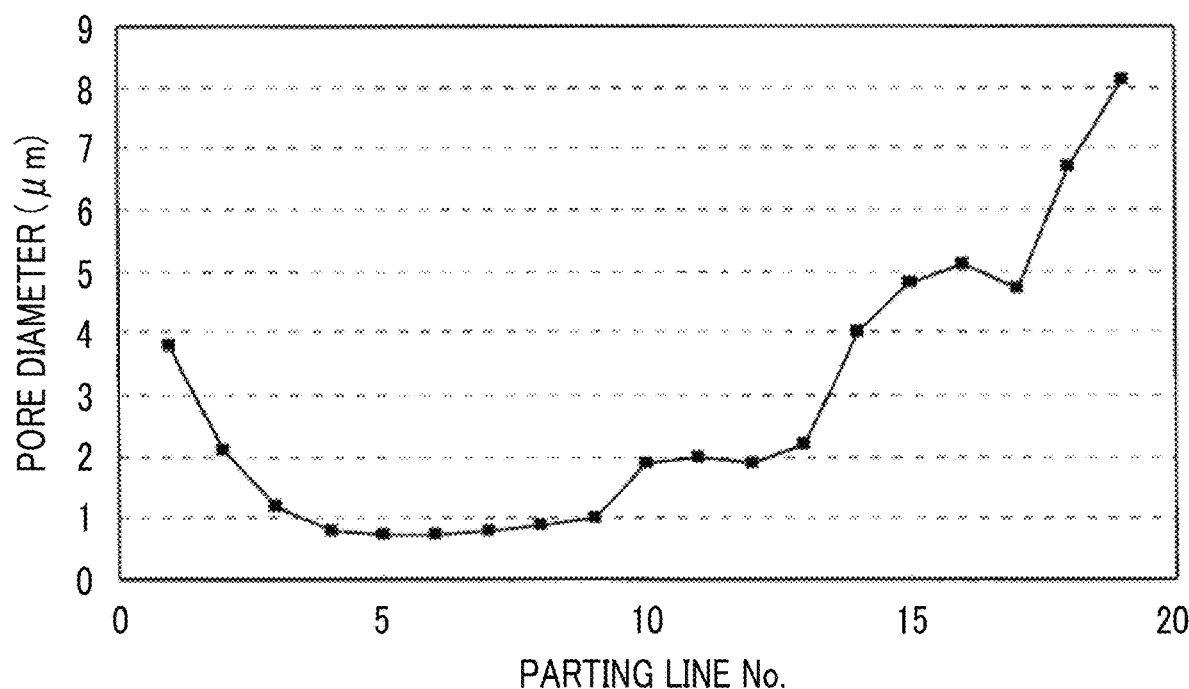
FIG. 8 is a graph showing distribution of an average pore diameter in a thickness direction of the porous membrane 15 (membrane for immunoisolation) obtained in Examples.

Each porous membrane obtained was impregnated with methanol and frozen in liquid nitrogen. Sections for cross section observation were cut out from the frozen porous membrane with a microtome (EM UC6 manufactured by Leica), and subjected to SEM imaging (SU8030 type FE-SEM manufactured by Hitachi High-Technologies Corporation). SEM imaging was performed at 3000 times. A photograph of a cross section of the porous membranes 14 and 15 is shown in FIGS. 4 and 7, respectively. In FIGS. 4 and 7, an upper side is a side exposed to air at the time of manufacture, and a lower side is a PET film side at the time of manufacture. 19 parting lines for dividing the SEM photograph of the cross section of each porous membrane into 20 from the upper side in the thickness direction are drawn, holes (closed hole) crossing or in contact with each parting line are traced with a digitizer, and therefore an average pore diameter of 50 consecutive holes was obtained. However, for a parting line in which pores were large and therefore only less than 50 pores could be measured, only available number of pores that could be counted in that parting line was measured. The obtained average pore diameter of each parting line was plotted in order from one surface to the other surface, and therefore distribution of the average pore diameter in the thickness direction of the membrane was obtained. Measurement results of the porous membranes 14 and 15 are shown in FIGS. 5 and 8, respectively. A portion in which an average pore diameter has a smallest parting line was used as a compact portion, and the average pore diameter of this portion was used as an average pore diameter of the compact portion. In addition, an average pore diameter of the parting line where an average pore diameter becomes maximum was obtained as a maximum pore diameter. Measured values are shown in Table 2.

Figure 6:
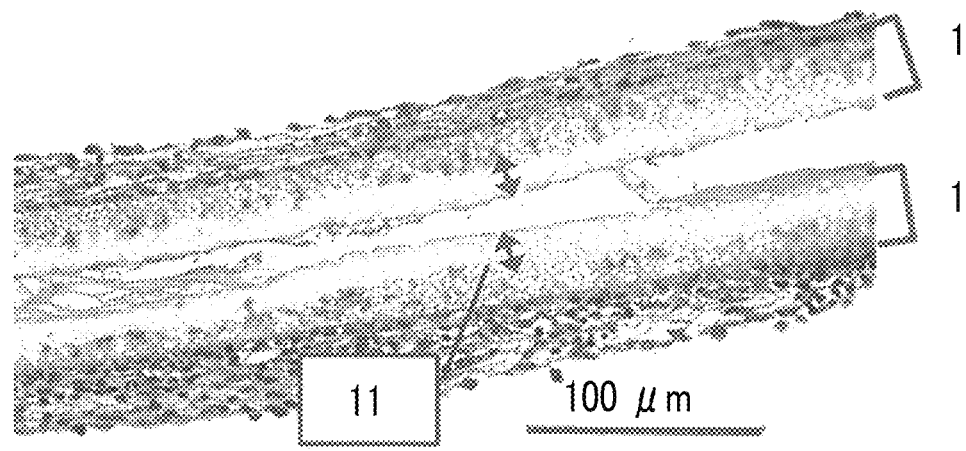
FIG. 6 shows an image of a histologically stained section containing the porous membrane 14 obtained in Examples.
Figure 9:
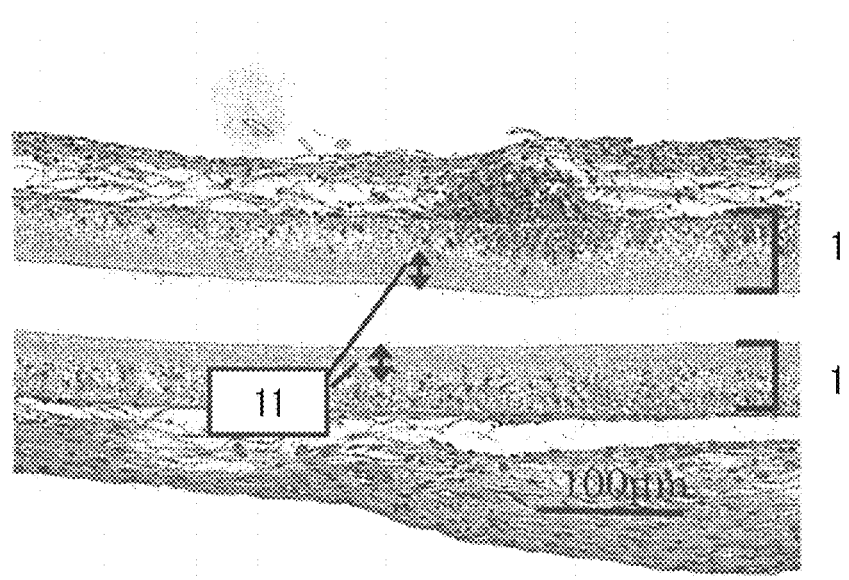
FIG. 9 shows an image of a histologically stained section containing the porous membrane 15 obtained in Examples.

In addition, in the same manner as in Examples 1 to 24 described above, evaluations were carried out on Examples 25 and 26 each having constitutions in which the porous membranes 14 and 15 were used, as shown in Table 2. The results are shown in Table 2. Furthermore, in the same manner as the porous membrane 1 except that two sheets were stacked in an envelope shape so as to be implanted, sections histologically stained with hematoxylin/eosin (HE) were prepared as described above. An image of a cross section of the site where the porous membrane was implanted was captured. FIGS. 6 and 9 show images of histologically stained sections each including the porous membranes 14 and 15.

TABLE 2

|  | Example 25 | Example 26 |
|---|---|---|
| Porous membrane | 14 | 15 |
| Location of compact portion | Inside | |
| Consecutiveness of pore diameter | Consecutive | Consecutive |
| Average pore diameter of compact portion (μm) | 0.8 | 0.8 |
| Average pore diameter of parting line on side where surface pore diameter is large (μm) | 6.0 | 8.9 |
| Anisotropy ratio | 7.5 | 11.1 |
| Direction of surface X | Permeation side | Permeation side |
| Insulin permeability | AA | AA |
| Cell infiltration inhibitory | A | A |
| Membrane durability | AA | AA |
| Membrane thickness | 50 | 83 |

EXPLANATION OF REFERENCES

1: porous membrane
11: humidity inhibiting layer

What is claimed is:

1. A membrane for immunoisolation, comprising:
a porous membrane that contains a polymer,
wherein the porous membrane includes a layered compact portion where a pore diameter is smallest within the membrane, and
a pore diameter continuously increases in a thickness direction from the compact portion toward at least one surface of the porous membrane,
wherein the porous membrane has a minimum pore diameter of 0.2 μm to 1.5 μm.

2. The membrane for immunoisolation according to claim 1, which is made from the porous membrane.

3. The membrane for immunoisolation according to claim 1, wherein the porous membrane has a minimum pore diameter of 0.2 μm to 1.3 μm.

4. The membrane for immunoisolation according to claim 1, wherein a ratio of a minimum pore diameter to a maximum pore diameter of the porous membrane is 3.0 to 20.0.

5. The membrane for immunoisolation according to claim 1, wherein the compact portion has a thickness of 0.5 μm to 30 μm.

6. The membrane for immunoisolation according to claim 1, wherein the porous membrane has a thickness of 10 μm to 250 μm.

7. The membrane for immunoisolation according to claim 1, wherein the porous membrane contains at least one kind of polysulfone and polyvinylpyrrolidone.

8. The membrane for immunoisolation according to claim 1, wherein the compact portion is located between any one surface X of the porous membrane and a portion at a distance of two-fifths the thickness of the porous membrane from the surface X,
wherein the surface X is the surface of the porous membrane closer to the compact portion.

9. The membrane for immunoisolation according to claim 1, wherein the compact portion is located between any one surface X of the porous membrane and a portion at a distance of one-third the thickness of the porous membrane from the surface X.

10. The membrane for immunoisolation according to claim 9, wherein a pore diameter continuously increases in the thickness direction from the compact portion toward at least a surface opposite to the surface X of the porous membrane.

11. The membrane for immunoisolation according to claim 10, wherein a pore diameter continuously increases in the thickness direction from the compact portion toward both surfaces of the porous membrane.

12. The membrane for immunoisolation according to claim 1, wherein the porous membrane comprises at least one kind of polysulfone, polyvinylpyrrolidone, and lithium chloride.

13. A chamber for transplantation for enclosing a biological constituent therein, the chamber comprising:
a membrane for immunoisolation on at least a part of a surface forming an inside and an outside of the chamber for transplantation,
wherein the membrane for immunoisolation comprises:
a porous membrane that contains a polymer,
wherein the porous membrane includes a layered compact portion where a pore diameter is smallest within the membrane, and
a pore diameter continuously increases in a thickness direction from the compact portion toward at least one surface of the porous membrane.

14. The chamber for transplantation according to claim 13,
wherein the compact portion is located between any one surface X of the porous membrane and a portion at a distance of two-fifths the thickness of the porous membrane from the surface X,
wherein the surface X is the surface of the porous membrane closer to the compact portion, and
wherein the surface X of the porous membrane is on the inside.

15. The chamber for transplantation according to claim 13, wherein the biological constituent is a cell.

16. A device for transplantation, comprising the chamber for transplantation according to claim 13 enclosing the biological constituent therein.

17. The device for transplantation according to claim 16, wherein the biological constituent releases a physiologically active substance.

18. The device for transplantation according to claim 17, wherein the physiologically active substance is insulin.

19. A method of transplantation of the biological constituent, comprising transplanting the device for transplantation according to claim 16 into a recipient.

20. A method of transplantation of insulin-secreting cells, comprising transplanting the device for transplantation according to claim 18 into a recipient.

* * * * *